(12) United States Patent
Niklason et al.

(10) Patent No.: US 7,943,378 B2
(45) Date of Patent: May 17, 2011

(54) TISSUE ENGINEERING

(75) Inventors: Laura E. Niklason, Hillsborough, NC (US); J. Andrew McKee, Durham, NC (US); Christopher M. Counter, Durham, NC (US)

(73) Assignee: Duke University, Durham, NC (US)

( * ) Notice: Subject to any disclaimer, the term of this patent is extended or adjusted under 35 U.S.C. 154(b) by 1332 days.

(21) Appl. No.: 10/388,588

(22) Filed: Mar. 17, 2003

(65) Prior Publication Data

US 2003/0235562 A1 Dec. 25, 2003

Related U.S. Application Data

(60) Provisional application No. 60/364,087, filed on Mar. 15, 2002.

(51) Int. Cl.
| | |
|---|---|
| C12N 15/63 | (2006.01) |
| C12N 5/00 | (2006.01) |
| C12N 5/08 | (2006.01) |
| A61F 13/00 | (2006.01) |
| A61K 48/00 | (2006.01) |

(52) U.S. Cl. ......... 435/455; 435/366; 435/395; 424/422

(58) Field of Classification Search .................. 435/455, 435/325; 424/93.1
See application file for complete search history.

(56) References Cited

U.S. PATENT DOCUMENTS

| | | | |
|---|---|---|---|
| 6,172,210 B1 | 1/2001 | Wiedmer et al. | |
| 6,245,566 B1 * | 6/2001 | Gearhart et al. | 435/384 |
| 6,399,384 B1 * | 6/2002 | Jat | 435/456 |
| 2002/0098166 A1 | 7/2002 | Havemann et al. | |
| 2002/0136726 A1 * | 9/2002 | Anderson et al. | 424/146.1 |
| 2003/0138945 A1 * | 7/2003 | McAllister et al. | 435/325 |
| 2003/0175961 A1 * | 9/2003 | Herron | 435/372 |
| 2004/0044403 A1 * | 3/2004 | Bischoff et al. | 623/1.41 |

FOREIGN PATENT DOCUMENTS

WO   WO 99/35245   *   7/1999

OTHER PUBLICATIONS

Robinson et al. Seeding of vascular grafts with an immortalized human dermal microvascular endothelial cell line. Angiology (1995) vol. 46(2), pp. 107-113 (abstract only).*
Robinson et al. Seeding of vascular grafts with an immortalized human dermal microvascular endothelial cell line. Angiology (1995) vol. 46(2), pp. 107-113.*
Niklason et al. Functional arteries grown in vitro. Science (1999) vol. 284, pp. 489-493.*
Berghella et al. Rversible immortalization of human myogenic cells by site-specific excision of a retrovirally transferred oncogene. Human Gene Therapy (1999) vol. 10, pp. 1607-1617.*
Efrat et al. Cell replacement therapy for type 1 diabetes. Trends in Molecular Medicine. 8(7):334-339, Jul. 2002.*
Dawson et al. Safety issues in cell-based intervention trials. Fertility and Sterility (2003) vol. 80(5), pp. 1077-1085.*
Poh et al. Blood vessels engineered from human cells. Lancet (Jun. 2005) vol. 365, p. 2122-2124.*
L'Heureux et al. (2001) "A human tissue-engineered vascular media: a new model for pharmacological studies of contractile responses." FASEB J. 15:515-524.*
Westerman et al. (1996) Proc. Natl. Acad. Sci. USA 93:8971-8976.*
Minamino et al. (2001) 21:3336-3342.*
Clontech Laboratories product information for pLNCX, published 2000, downloaded from http://clontech.com/images/pt/dis_vectors/PT3133-5.pdf Feb. 1, 2008.*
Krump-Konvalinkova et al, "Generation of Human Pulmonary Microvascular Endothelial Cell Lines", Laboratory Investigation 81(12):1717-1727 (2001).
Chen et al, "Production and Characterization of Human 293 Cell Lines Expressing the Site-Specific Recombinase Cre", Somatic Cell and Molecular Genetics 22(6):477-488 (1996).
Eaton et al, "Immortalized Chromaffin Cells Disimmortalized with Cre/lox Site-Directed Recombination for Use in Cell Therapy for Pain after Partial Nerve Injury", Experimental Neurology 175:49-60 (2002).
Niklason et al, "Morphologic and mechanical characteristics of engineered bovine arteries", J. Vasc. Surg. 33:628-638 (2001).
Cao et al. "Telomerase activation causes vascular smooth muscle cell proliferation in genetic hypertension", FASEB Journal 16(1):96-98 (2002).
Minamino and Kourembanas, "Mechanisms of Telomerase Induction During Vascular Smooth Muscle Cell Proliferation", Circ. Res. 89:237-243 (2001).
Yang et al, "Human Endothelial Cell Life Extension by Telomerase Expression", The Journal of Biological Chemistry 274(37):26141-26148(1999).
Niklason et al, "Lifespan extension in vascular tissue engineering", In Vitro Cellular And Developmental Biology Animal 38(Abstract):4A (2002) & 2002 Congress On in Vitro Biology, Orlando, FL, USA, Jun. 25-29, 2002.
Niklason et al, "Functional Arteries Grown In Vitro", Science 284:489-493 (1999).
L 'Heureux et al, "A completely biological tissue-engineered human blood vessel", FSEB J. 12;47-56 (1998).
Klinger et al,. "Relevance and safety of telomerase for human tissue engineering", PNAS 103(8):2500-2505 (2006).
L'Heureux et al, "Human Tissue Engineered Blood Vessel for Adult Arterial Revascularization", Nat. Med. 12(3):361-365 (2006).
Schechnar et al, "In vivo formation of complex microvessels lined by human endothelial cells in an immunodeficient mouse", PNAS 97(16):9191-9196 (2000).
Koike et al, "Tissue engineering: creation of long-lasting blood vessels", Nature 428(6979):138-9 (2004)—Abstract.
McKee et al. "Human arteries engineered in vitro", EMBO reports 4(6):633-638 (2003).
Procol_Approval2.pdf file.
Koike et al, "Creation of long-lasting blood vessels", Nature 428:138-139 (2004).

(Continued)

*Primary Examiner* — Quang Nguyen
(74) *Attorney, Agent, or Firm* — Nixon & Vanderhye P.C.

(57) ABSTRACT

The present invention relates, in general, to tissue engineering and, in particular, to a method of extending the lifespan of cells suitable for use in vascular engineering.

20 Claims, 5 Drawing Sheets

OTHER PUBLICATIONS

Wang et al, "Risky immortalization by telomerase", Nature 405:755-756 (2000).

Cao et al, "Telomerase activation causes vascular smooth muscle cell proliferation in genetic hypertension", The FASEB Journal express article 10.1096/fj.01-0447fje, Published online Nov. 14, 2001.

Urano et al, "Vascular smooth muscle cell outgrowth, proliferation, and apoptosis in young and old rats", Atherosclerosis 146:101-105 (1999).

Noble et al, "Alterations in the $p16^{INK4a}$ and p53 tumor suppressor genes of hTERT-immortalized human fibroblasts", Oncogene 23:3116-3121 (2004).

Bennett et al, "Cooperative Interactions Between RB and p53 Regulate Cell Proliferation, Cell Senescence, and Apoptosis in Human Vascular Smooth Muscle Cells From Atherosclerotic Plaques", Circ. Res. 82:704-712 (1998).

* cited by examiner

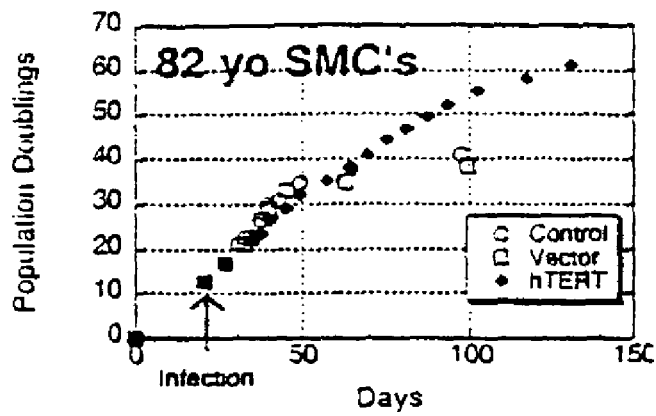
Fig 4: Growth curves of SMC's derived from an elderly donor. Saphenous vein-derived SMC's exhibit extended lifespan after infection with hTERT. Control and Vector populations both stop replicating at 40 PD's.
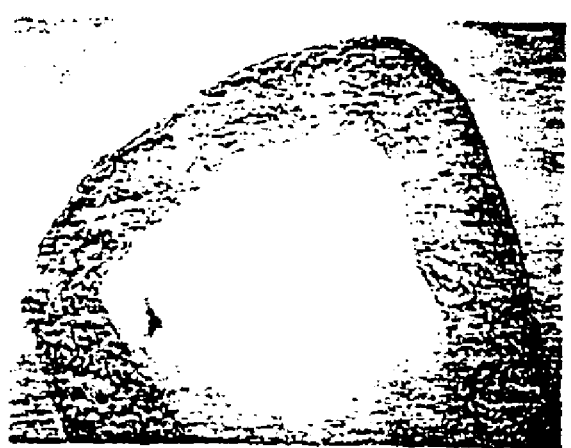
Fig. 5: Human vessel from 82 yo SMC's. Rupture strength < 25 mm Hg.

TISSUE ENGINEERING

This application claims priority from Provisional Application No. 60/364,087, filed Mar. 15, 2002, the entire content of that application being incorporated herein by reference.

TECHNICAL FIELD

The present invention relates, in general, to tissue engineering and, in particular, to a method of extending the lifespan of cells suitable for use in vascular engineering.

BACKGROUND

In the United States, 1.4 million patients per year undergo operations requiring arterial prostheses (Langer et al, Science 260:920-926 is (1993)). Approximately 100,000 patients per year require vascular bypass of small caliber arteries, but have no usable autologous artery or vein for grafting (Niklason, Science 286:1493-1494 (1999)). Hence, there is a pressing need for autologous vessels to treat atherosclerotic disease (Lefkowitz et al, Journal of American Medical Association 285:581-587 (2001)). Arteries have been successfully engineered from neonatal human smooth muscle cells (SMCs) (L'Heureux et al, FASEB J. 12:47-56 (1998)), and from porcine and bovine SMCs (Niklason et al, Science 284:489-493 (1999), Niklason et al, Journal of Vascular Surgery 33:628-638 (2001)). However, these approaches have not yet been translated to the growth of human arteries suitable for clinical use.

The inability of non-neonatal SMCs to form arteries in vitro may be due to their finite lifespan in culture. Specifically, arterial culture in vitro requires 45 to 60 population doublings (PD) of SMCs to produce a mechanically robust artery, while endothelial monolayer formation requires far fewer cell doublings (L'Heureux et al, FASEB J. 12:47-56 (1998), Niklason et al, Science 284:489-493 (1999), Niklason et al, Journal of Vascular Surgery 33:628-638 (2000)). However, non-neonatal human SMCs proliferate in vitro for only 15 to 30 PD before terminally growth arresting in a state termed senescence (Bierman, In Vitro 14:951-955 (1978), Bonin et al, Arteriosclerosis, Thrombosis, and Vascular Biology 19:575-587 (1999)). Hence, the limited lifespan of human SMCs represents a fundamental hurdle to the culture of autologous blood vessels.

Recently, numerous genetic approaches have been developed to extend the lifespan of human somatic cells. For instance, in several normal human somatic cells, expression of the hTERT gene (Nakamura et al, Cell 92:587-590 (1998)) (hTERT being the catalytic protein subunit of human telomerase reverse transcriptase) has been shown to reactivate telomerase, the enzyme that elongates chromosome-capping telomeres (Sedivy, Proceedings of the National Academy of Sciences USA 95:9078-9081 (1998)). Cellular lifespan was extended without induction of a cancerous phenotype (Jiang et al, Nature Genetics 21:111-114 (1999), Morales et al, Nature Genetics 21:115-118 (1999)), Yang et al, Journal of Biological Chemistry 274:26141-26148 (1999)).

The present invention results from studies demonstrating that expression of lifespan-extending genes in non-neonatal human cells (i.e., SMCs) extends the proliferative capacity of these cells. Approaches utilizing lifespan extension make possible the culture of robust arteries from human cells in vitro.

SUMMARY OF THE INVENTION

The present invention relates generally to tissue engineering. More specifically, the invention relates to a method of extending the lifespan of cells and to the use of such cells in the production of vascular grafts.

Objects and advantages of the present invention will be clear from the description that follows.

BRIEF DESCRIPTION OF THE DRAWINGS

FIG. 1A. TRAP assay, hTERT SMCs (hT) were positive for telomerase activity, as indicated by 6 bp laddered products, while normal SMCs (n) and vector SMCs (v) were negative. HEK cells expressing hTERT (Armbruster et al, Molecular and Cellular Biology 21:7775-7786 (2001)) served as a positive control (CTL). HI, heat-inactivated controls; asterisk, PCR internal control. FIG. 1B. Normal (n) and vector SMCs (v) senesced at 37 PD, while hTERT SMCs (hT) grew to at least 100 PD. Population doubling time is preserved. FIG. 1C. Southern hybridization demonstrates telomere erosion of normal and vector SMCs, while the telomeres of hTERT SMCs are extended for at least 80 PD.

FIG. 2B, pRb; SC, subconfluent; C, confluent; FIG. 2C, p53; +, cells treated with UV irradiation; and FIG. 2D, the c-myc protein.

FIG. 3E; vWF immunostaining reveals a confluent monolayer of HUVEC on the lumen (asterisk) of a hTERT SMC artery. FIG. 3F; Western blots of hTERT SMC arteries (n=4) show expression of normal SMC markers, similar to normal SMC-derived vessels (n=4). Scale bars: 0.5 mm in 1A, 1B; 100 µm in 1C-1E.

FIG. 4. Growth curves of SMCs derived from 82 year old donor. Saphenous vein-derived SMCs exhibit extended lifespan after infection with hTERT. Control and Vector populations both stop replicating at 40 PD's.

FIG. 5. Human vessel from 82 year old SMCs. Rupture strength <25 mmHg.

FIG. 6A. Tissue engineered vessel using control vascular SMC and EC from a 47 year old donor. FIG. 6B. Vessel cultured under identical conditions, using cells from 47 year old donor expressing hTERT. FIG. 6C. Vessel cultured from 67 year old donor. FIG. 6D. Vessel cultured from cells from 67 year old donor, expressing hTERT.

DETAILED DESCRIPTION OF THE INVENTION

Figure 1:
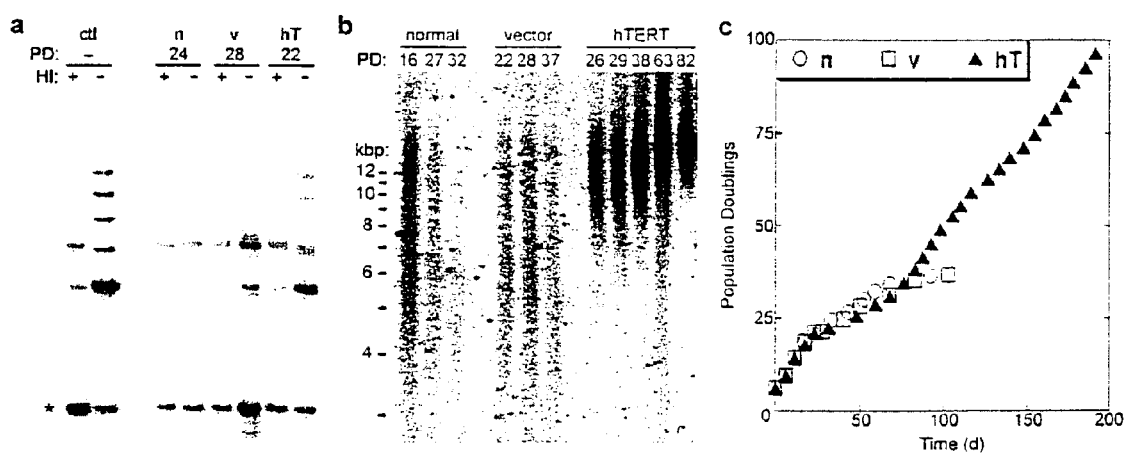
FIGS. 1A-1C. Telomerase in SMCs increases lifespan and extends telomeres.

The present invention relates to a method of producing vascular grafts. The method comprises introducing into cells an expression vector that comprises a nucleic acid sequence encoding a lifespan extending and/or immortalizing gene, or functional portion or variant thereof, under conditions such that the sequence is expressed and the protein product of the gene, or functional portion or variant thereof, is produced. These cells can then be employed in the engineering of vascular grafts.

Cells suitable for use in the invention include SMCs, epithelial cells (of which endothelial cells (ECs) are a subset), fibroblasts, pericytes, cardiomyocytes, and nervous system cells. The cells can be fully differentiated vascular cells isolated from an individual. Alternatively, the cells can be derived from stem cells or progenitor cells that are cultured under conditions such that they differentiate into vascular cells. Advantageously, the cells are human cells derived from the graft recipient. Typically, the cells are non-neonatal SMCs derived from an individual of any age.

Cells can be harvested from a patient from a peripheral arterial or venous branch biopsy. The biopsy can be conducted anywhere on the patient's body that allows access to peripheral vasculature; the upper arm and lower leg are two examples. The surgical technique used can be that described for temporal artery biopsy (Albertini et al, Dermatalogic Surgery 25:501-508 (1999)). Doppler ultrasound or other means of imaging the vasculature (such as digital subtraction angiography) can be used to locate the peripheral vessel segment of interest. Under local anesthetic, the skin, cutaneous fat, and other fascia can be dissected to expose the blood vessel. The vessel segment can be sutured closed on both sides, then excised (Albertini et al, Dermatalogic Surgery 25:501-508 (1999)). As described (Ross, Journal of Cellular Biology 50:172-186 (1971), (Niklason et al, Science 284: 489-493 (1999), Niklason et al, Journal of Vascular Surgery 33:628-638 (2001)), the vessel can then be processed for isolation of vascular ECs, SMCs and any other vascular cells, if necessary, such as adventitial fibroblasts.

In the case of ECs, the blood vessel can be cut axially through one wall (under sterile conditions in a tissue culture dish), exposing the inner lumen. This EC-coated lumen can be lightly scraped to obtain ECs that can then be used to establish EC cultures in sterile flasks. When SMCs are sought, the lumen and intima can then be scraped away, and the exposed medial layer inverted face-down. If present, an outermost adventitial layer (containing fibroblasts) can be removed. With the addition of SMC culture medium, SMCs can migrate from the blood vessel wall onto the tissue culture surface. After 7 d, the vessel tissue can be removed from culture, leaving only vascular SMCs. In this manner, cultures of ECs and SMCs from a human donor can be established for use in the invention.

An example of an EC culture medium includes, but is not limited to, EGM-2 (BioWhittaker, Walkersville, Md.) lacking ascorbic acid and hydrocortisone supplement aliquots, but supplemented with 150 µg ml$^{-1}$ heparin. An example of SMC culture medium includes, but is not limited to, SMGM-2 medium (BioWhittaker) supplemented with 10-20% fetal bovine serum, proline, glycine, and ascorbic acid at 50 µg m$^{-1}$, and alanine at 20 µg ml$^{-1}$.

Stem and progenitor cells, also suitable for use in the invention, can be isolated from a tissue biopsy and cell sorted (e.g., by flow cytometric/fluorescence techniques), if necessary, and then directed into vascular lineages via specific culture conditions including, but not limited to, medium supplements (growth factors, vitamins), growth substrates, mechanical stress-strain environment, medium conditioned by other cell cultures, and/or co-culture with other cell types. A recent example of this approach involves purifying ECadherin$^-$/flkl$^+$ cells from undifferentiated, ECadherin$^+$ human embryonic stem cells, and then directing these progenitors into vascular cell lineages (Yamashita et al, Nature 408:92-96 (2000)). Further, endothelial progenitor cells can be isolated from circulating blood of a graft recipient, and maintained as progenitors or directed into an endothelial cell lineage by culture conditions (Asahara et al, Science 275:964-967 (1997)).

Numerous encoding sequences can be employed to lifespan extend and/or immortalize normal human cells. Examples of encoding sequences include wild-type or altered genetic material imparted by viruses including, but not limited to, simian virus 40 (encoding large T antigen and other products), human papilloma virus (encoding E6 and E7 proteins and other products), adenovirus (encoding E1A protein and other products), and Epstein-Barr virus. Encoding sequences suitable for use in the invention also include normal cellular genes exhibiting altered transcription and/or function, such as myc, c-jun, c-ras, v-src, Mdm2, p53-encoding gene, and p21-encoding gene (Katakura et al, Methods in Cell Biology, Mather J P, ed, 57:69-91 (1998), Sedivy, Proceedings of the National Academy of Sciences USA 95:9078-9081 (1998)). Encoding sequences suitable for use in the present invention further include nucleic acid sequences encoding a protein having telomerase catalytic activity. Advantageously, the nucleic acid sequence encodes the catalytic protein subunit of human telomerase reverse transcriptase (hTERT) (GENBANK DNA accession #AH007699; GENBANK protein sequence accession #BAA74724), or functional portion or variant thereof. Examples of such portions/variants are given in U.S. Pat. Nos. 5,770,422, 5,917,025, 6,093,809, 6,166,178, 6,261,836, 6,309,867, and 6,337,200. Any of the above nucleic acid sequences can be prepared chemically or recombinantly using standard techniques.

The encoding sequences of the invention can extend the lifespan of the cells into which they are introduced without inducing a tumorogenic phenotype (as defined by genomic instability, cell growth in the absence of mitogens, lack of contact inhibition and/or anchorage independent growth). These cells become constituents of vascular grafts.

Recent evidence has demonstrated the utility of the above sequences in lifespan-extending and/or immortalizing human vascular cells. To immortalize or lifespan-extend ECs, reports have described the successful use of telomerase (Yang et al, Journal of Biological Chemistry 271:26141-26148 (1999)), simian virus 40 (Ades et al, Journal of Investigative Dermatology 99:683-690 (1992)), human papilloma virus (Rhim et al, Carcinogenesis 19:673-681 (1998)), E2F overexpression (Spyridopoulos et al, Circulation 98:2883-2890 (1998)), and Bcl-2 (Schechner et al, Proceedings of the National Academy of Sciences USA 97:9191-9196 (2000)). Described approaches to extend lifespan or immortalize SMCs have reported use of human papilloma virus (Perez-Reyes et al, Proceedings of the National Academy of Sciences USA 89:1224-1228 (1992), Bonin et al, Arteriosclerosis, Thrombosis and Vascular Biology 19:575-587 (1999)) and simian virus 40 (in bovine SMCs) (Westerman et al, Proceedings of the National Academy of Sciences USA 93:8971-8976 (1996)).

One or more encoding sequence of the invention (e.g., a hTERT encoding sequence) can be present in an expression construct, advantageously in operable linkage with a promoter. The construct can also include one or more drug resistance gene (e.g., hygromycin). The drug resistance gene can be operably linked to the same promoter driving expression of the lifespan extending sequence. High transcription rate promoters are preferred, such as any viral promoter (e.g., SV40) or a tetracycline-inducible promoter (see below). In addition, constructs of the invention can incorporate restriction enzyme sites for gene splicing, bacterial drug resistance genes (such as for ampicillin resistance), for example, to facilitate large scale preparation of the construct in bacteria, and other sequences (e.g., 3' and 5' long terminal repeats (LTRs), and ψ packaging sequences) that facilitate compatibility of the construct with appropriate viral vector packaging cell lines (if applicable). Such constructs can be designed per standard nucleic acid techniques and/or obtained commercially. Examples include the pFB and pFB-neo vectors, compatible with Moloney murine leukemia virus packaging cell lines (Stratagene, La Jolla, Calif.).

Constructs of the invention can further incorporate upstream genetic material that renders the transcription of downstream genetic material (such as one of the lifespan-extending sequences described above) to be repressible, inducible, or excisable. As an example of repressible transduction constructs, the tetracycline-controlled transactivator (tTA) system can be used upstream of, for example, the hTERT gene, providing hTERT transcription only in the absence of tetracyclines (Baron et al, Nucleic Acids Research 25:2723-2729 (1997)). As an example of an inducible system, the reverse tTA (rtTA) system can be used, providing transcription of, for example, hTERT only when a tetracycline is present (Gossen et al, Science 268:1766-1769 (1995)). Also, these promoters can be modified, resulting in an increase or decrease in the strength of transcription by approximately 4 orders of magnitude in either direction (Baron et al, Nucl. Acids Res. 25:2723 (1997); Grossen et al, Science 268:1766 (1995)). In the case of an excisable construct, an approach such as the Cre-Lox system can be used to allow expression of the construct until Cre recombinase is added to remove this genetic material from cell genomes (Westerman et al, Proceedings of the National Academy of Sciences USA 93:8971-8976 (1996)). An excisable constructs containing lifespan-extending genetic material (coding for simian virus 40 large T antigen) has been shown to reversibly immortalize bovine vascular SMCs (Westerman et al, Proceedings of the National Academy of Sciences USA 93:8971-8976 (1996)).

The expression constructs of the invention can be introduced into SMCs, ECs, or any other cell type, to provide constituent cells of vascular tissue (e.g., artery, vein, arteriole, venule or capillary), using any of a variety of approaches, which can vary with the nature of the construct employed.

One approach is to utilize viral vectors to introduce constructs, as described above. Numerous viral vectors can be designed that lack genes that normally provide for replication (such as the gag and pol genes, for retroviruses), so that these viruses can stably infect target cells (leading to expression of the genetic construct) but not subsequently replicate. These "replication-incompetent" viral vectors can be produced to high yield by using packaging cells, that house the genes necessary for replication that are lacking in the viruses, thereby enabling high level production of replication-incompetent virus. Vectors that can be used include, but are not limited to, retroviral, lentiviral, adeno-associated, and adenoviral vectors (Pasi, British Journal of Haematology 115:744-757 (2001), Somia et al, Nature Reviews. Genetics 1:91-99 (2000)).

Non-viral delivery methods can also be used. Such methods to transduce genetic constructs into cells include, but are not limited to, the use of liposome-encapsulated constructs, polymer-encapsulated constructs, receptor-mediated transfer of such encapsulated constructs, polymer-complexed constructs, constructs incorporated by electroporation, constructs incorporated by calcium phosphate precipitation, and naked constructs (Templeton et al, Gene Therapy: therapeutic mechanisms and strategies, New York (2000), Pasi, British Journal of Haematology 115:744-757 (2001)).

Cells genetically modified by construct-containing vectors, as described above, can be maintained in culture and selected, for example, for the presence of drug resistance. To determine a drug concentration sufficient to select cultures for drug resistance, normal cells can be exposed to different drug concentrations, then cultured, for example, for at least 2 weeks to determine a minimal "kill dose" that avoids unnecessarily high drug concentrations.

Engineered blood vessels can be constructed by a variety of methods (for instance, see Niklason et al, Science 284:489-493 (1999)) using constituent cells prepared as described above. These approaches include (1) seeding constituent cells on tubular gels of denatured collagen, (2) culturing sheets of constituent cells, then rolling these sheets concentrically into a tube, and (3) culturing constituent cells on a degradable synthetic tubular scaffold under conditions of pulsatile stress. Such techniques can be extended to culture cells on biological scaffolds of in vivo origin (e.g., fibrillar (non-denatured) porcine collagen) or in vitro origin (e.g., extracellular matrix of decellularized, tissue engineered human vascular tissue) (Niklason et al, Science 284:489-493 (1999)).

Tissue engineered blood vessels in accordance with the invention can be used as vascular grafts, and as such, can be implanted using standard surgical techniques currently used in procedures such as coronary and peripheral revascularizations.

Certain aspects of the invention can be described in greater detail in the non-limiting Examples that follows.

EXAMPLE 1

Experimental Details

Cells. Human aortic SMCs isolated from a 2 year old male (BioWhittaker) were received at passage 5 and PD 6. Cells were propagated in SMGM-2 (BioWhittaker) with 10-20% fetal bovine serum, proline, glycine, and ascorbic acid at 50 µg ml$^{-1}$, and alanine at 20 µg ml$^{-1}$. SMCs were infected using amphotropic retroviruses containing the plasmid pBABE-Hygro-hTERT (hTERT) or pBABE-Hygro (Vector) (Hahn et al, Nature 400:464-468 (1999)). Infected cells were selected continuously at 60 µg ml$^{-1}$ hygromycin. Human embryonic kidney (HEK) cells expressing hTERT were previously described (Armbruster et al, Molecular and Cellular Biology 21:7775-7786 (2001)). HUVEC were cultured in EGM-2 (excluding hydrocortisone and ascorbic acid; Biowhittaker) supplemented with 10% FBS and 150 µg ml$^{-1}$ heparin (GIBCO-BRL). Surplus saphenous veins (otherwise discarded) were harvested from patients undergoing revascularization procedures.

Telomerase activity and visualization of telomeres. As described (Armbruster et al, Molecular and Cellular Biology 21:7775-7786 (2001)), 1.0 µg of lysates were isolated from SMCs and assayed for telomerase activity, after which the resultant radiolabeled PCR products were separated on a 12% polyacrylamide gel, which was then dried and exposed to a phosphorimager screen as described (Kim et al, Nucleic Acids Research 25:2595-2597 (1997)). As specificity controls, duplicate lysates were heat-inactivated for 2 min at 85 C. To visualize telomere restriction fragments, 1 µg of genomic DNA was HinF1- and Rsa1-digested, and then resolved on a 0.5% agarose gel. The gel was dried for 30 min at 64 C, hybridized to a $^{32}$P-labeled (CCCTAA)$_3$ probe at 37 C overnight, rinsed 3 times in 15×SSC, and then exposed to a phosphorimager screen as described (Counter et al, EMBO J. 11:1921-1929 (1992)).

Blood vessel culture and endothelialization. Blood vessel bioreactors, pulsatile flow system, and PGA meshes (3 mm internal diameter, 8 cm length) were prepared as described (Niklason et al, Science 284:489-493 (1999), Niklason et al, Journal of Vascular Surgery 33:628-638 (2000)). For each engineered blood vessel, SMCs were seeded onto tubular PGA scaffolds (normal SMCs: 11×10$^6$ cells, passage 10 PD 20; hTERT SMCs: 8×10⁶ cells, passage 11, PD 32, or 9 PD post-infection). Bioreactors were filled with culture medium and meshes were pulsed internally via silicone tubing (165 bpm, 1% radial distension), with humidification and 10% $CO_2$ at 37 C. hTERT SMCs vessels were cultured without hygromycin selection, because preliminary experiments showed that hygromycin partially inhibited protein synthesis, despite the presence of the resistance gene. Blood vessels were endothelialized by removing the inner silicone tubing, injecting 3.6×10⁶ HUVEC at passage 2, and allowing the cells to adhere for 16 hours with periodic rotation.

Mechanical Testing and Calculations. Vessel mechanics were quantified using a circumferential-stretch test, similar to that described previously (Seliktar et al, Annals of Biomedical Engineering 28:351-362 (2000), Donovan et al, Journal of Vascular Surgery 12:531-537 (1990)). Two wires were inserted through the lumen of a vessel segment, to which increasing tension was applied. The distending vessel was imaged using a high resolution digital video camera with a 10 μm pixel size (XL1, Canon), and the external radius was quantified using Adobe Photoshop and NIH Image. Circumferential wall stress was calculated from $\sigma = F (2l(r_e - r_i))^{-1}$, where σ is the stress, l is the vessel segment length, $r_e$ is the external radius, $r_i$ is the internal radius, and F is the stretching force. Wall area (A) from each cross sectional image was used to calculate $r_i$, from $A = \pi(r_e^2 - r_i^2)$, and to calculate the average wall thickness. Theoretical rupture strength (pressure, P) was calculated from the thick-walled pressure vessel equation for circumferential stress (Pagani et al, Circulation Research 44:420-429 (1979)):

$$\sigma = P \frac{\left( r_i^2 + \frac{4(r_i r_e)^2}{(r_i + r_e)^2} \right)}{(r_e^2 - r_i^2)} \quad (1)$$

Western blot analysis. For pRb blots, duplicate cell cultures were seeded at identical density, and then collected and solubilized at 3 days (subconfluent) or 7 days (confluent) (Jiang et al, Nature Genetics 21:111-114 (1999), Morales et al, Nature Genetics 21:115-118 (1999)). For p53 blots, one of two duplicate subconfluent cultures was subjected to 6 Gy of irradiation over 1.2 min (Morales et al, Nature Genetics 21:115-118 (1999)). After 4 hours, cells were solubilized for blotting. Blots with lysates from cultured cell pellets and vessel samples were performed per standard techniques using primary antibodies to β-actin, calponin, tropoelastin (Sigma), SM-MHC (Biomedical Technologies), hyper-phosphorylated pRb (Cell Signaling Technology), p53 and c-myc (Santa Cruz) (Wang et al, Nature 405:755-756 (2000)).

Immunostaining. Vessel samples were fixed in formalin, dehydrated, and embedded in paraffin. 5 μm sections were deparaffinized and then immunostained for the presence of proliferating cell nuclear antigen (PCNA; DAKO) (Niklason et al, Science 284:489-493 (1999)), DNA strand breaks (Apoptag Apoptosis Detection Kit, Intergen), or von Willebrand Factor (vWF; DAKO) per the manufacturers' instructions.

Cell density (DNA) analysis. As described (Niklason et al, Science 284:489-493 (1999)), vessel samples were weighed and lyophilized to obtain wet and dry weights, respectively. The samples were incubated in papain (1 ml; 0.7 μg ml⁻¹) at 60 C overnight. 2 ml of Hoechst dye (Polysciences) was added to each sample, which was then analyzed in a spectrofluorimeter ($\lambda_{365}$ excitation, $\lambda_{458}$ emission) calibrated to calf thymus DNA standards.

Collagen analysis. As described (Niklason et al, Science 284:489-493 (1999)), papain-digested samples (see above) were incubated in 6 N HCl at 115 C for 18 h, neutralized, reacted with p-dimethylaminobenzaldehyde and chloramine-T, then quantified at $\lambda_{555}$. A 1:10 weight ratio of hydroxyproline:collagen was used. For all comparisons, a student's t-test was calculated using Microsoft Excel.

Results

Normal SMCs isolated from aortic tissue of a child donor were stably infected with either a control retroviral vector or one encoding hTERT, after which polyclonal populations were selected for resistance to the hygromycin marker of the vector. Telomerase activity was restored in the hTERT-expressing SMC (hTERT SMC) cultures, but not in uninfected or vector controls, since only hTERT SMC extract produced 6 bp heat sensitive ladder products when incubated with a telomeric primer (FIG. 1A).

Reactivation of telomerase activity also arrested telomere shortening and extended the lifespan of hTERT SMCs. Specifically, Southern analysis revealed that the telomere-containing terminal restriction fragments of uninfected or vector control SMCs decreased over time, arresting at a length of ~6 kbp, consistent with the length of telomeres of other senescent cells (FIG. 1C) (Harley et al, Cold Spring Harbor Symposia on Quantitative Biology 59:307-315 (1994)). Correspondingly, these cells had a finite lifespan, reaching senescence at ~PD 37. In contrast, the telomeres of hTERT SMCs increased over time. hTERT SMCs proliferated over 100 PD, more than twice the lifespan of the control SMC cultures, and long enough to theoretically generate an artery in vitro (FIG. 1B).

Figure 2:
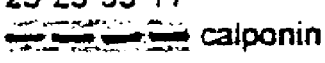
FIGS. 2A-2D. hTERT SMCs (hT) display a normal, non-transformed phenotype as compared to normal SMCs (n) and vector SMCs (v). Western blots for FIG. 2A, calponin and smooth muscle myosin heavy chains (differentiation markers) and tropoelastin (extracellular matrix protein)

The hTERT SMCs were phenotypically indistinguishable from normal SMCs. hTERT SMCs retained a normal hill and valley morphology and striated cell bodies beyond 100 PD, comparable to normal SMCs at early passage. Late passage hTERT SMCs also exhibited a differentiated phenotype similar to control SMCs, retaining expression of SMC-characteristic proteins such as calponin (intermediate differentiation marker), smooth muscle myosin heavy chains (SM-MHC; advanced differentiation marker), and tropoelastin (extracellular matrix protein) (FIG. 2A).

Telomerase is activated in most cancer cells (Shay et al, European Journal of Cancer 33:787-791 (1997)) and the forced expression of hTERT in normal human cells is known to contribute to the tumourigenic process (Hahn et al, Nature 400:464-468 (1999), Elenbaas et al, Genes & Development 15:50-65 (2001), Rich et al, Cancer Research 61:3556-3560 (2001)), raising the possibility that hTERT expression in SMCs could theoretically predispose the cells to a transformed phenotype. It was therefore determined whether hTERT SMCs exhibit transformed phenotypes. Normal cells de-phosphorylate the retinoblastoma protein (pRb) to prevent entry into S phase, whereas many tumor cells escape this block by keeping pRb constitutively hyper-phosphorylated (Lundberg et al, European Journal of Cancer 35:531-539 (1999)). In hTERT SMCs at high cell densities, hyper-phosphorylated pRb was down-regulated, similar to normal and vector SMCs (FIG. 2B). Normal cells also up-regulate the protein p53 to halt proliferation in response to DNA damage, whereas many tumor cells lose this response (Lundberg et al, European Journal of Cancer 35:531-539 (1999)). DNA damage from ultraviolet (UV) irradiation stimulated up-regulation of p53 in hTERT SMCs similar to controls (FIG. 2C). These results indicate that hTERT SMCs retain normal cell-cycle regulators in response to contact inhibition and DNA damage, both of which are hallmarks of a non-transformed phenotype. Lastly, although it was recently reported that c-myc was activated in a single hTERT expressing cell line (Wang et al, Nature 405:755-756 (2000)), late passage hTERT SMCs did not exhibit altered c-myc protein expression (FIG. 2D). Thus, by multiple criteria the hTERT SMCs behave identically to their uninfected counterparts and show no signs of transformation.

Figure 3:
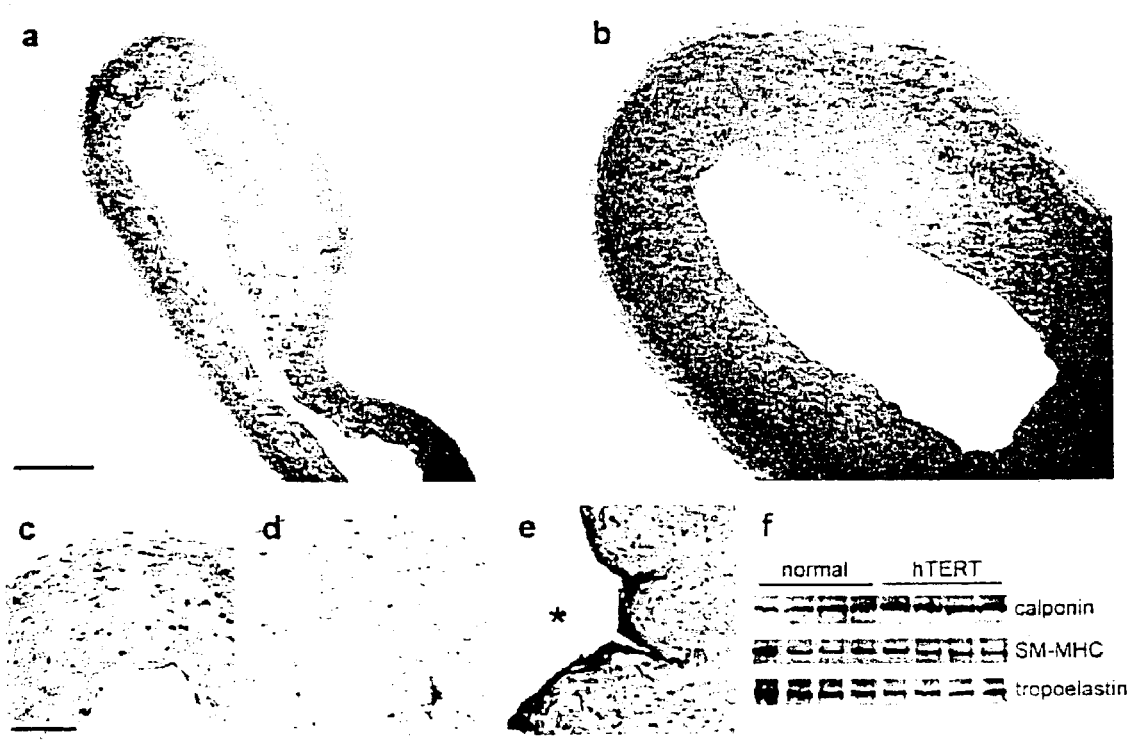
FIGS. 3A-3F. Representative tissue engineered human arteries, 3 mm internal diameter. Hematoxylin and eosin stain of normal SMCs (FIG. 3A) and hTERT SMC (FIG. 3B) blood vessels. TUNEL staining of normal SMC vessels shows widespread cell death (FIG. 3C) in contrast to hTERT SMC vessels (FIG. 3D); dark nuclei are positive.

To determine the impact of hTERT in human vascular tissue engineering, blood vessels were cultured using a biomimetic system as previously described (Niklason et al, Science 284:489-493 (1999), Niklason et al, Journal of Vascular Surgery 33:628-638 (2000)). Normal or hTERT SMCs were seeded onto a tubular scaffolding of degradable polyglycolic acid (PGA), and cultured under pulsatile pressure in bioreactors. Human vessels were grown from normal SMCs (n=4) and hTERT SMCs (n=4). After 7 weeks, the hTERT SMCs blood vessels were luminally seeded with human umbilical vein endothelial cells (HUVEC) for 16 hours. Adhesion and phenotype of HUVEC was verified by the luminal presence of cells positive for von Willebrand Factor (vWF) (FIG. 3E). Normal SMCs blood vessels were not seeded with HUVEC, because they were extremely fragile and could not be manipulated.

The physical and histologic appearance of hTERT vessels was dramatically improved compared to control SMCs vessels (FIGS. 3A and 3B). Wall thickness of hTERT vessels was significantly greater than controls (P<0.01), and was similar to that of native artery (Table 1). hTERT vessels also had greater cellular density and significantly greater rupture strengths than control vessels (356±64 mm Hg for hTERT, vs. 59±55 mm Hg for controls, P<0.0005). Increased wall thickness and cellularity likely imparted increased strength to hTERT vessels, since the collagen contents of hTERT and control vessels were similar (Table 1). Thus, hTERT expression enabled culture of arteries that were architecturally and mechanically far superior to those derived from control SMCs.

TABLE 1

Physical characteristics of engineered human blood vessels.

| | Engineered Human Vessels: | | Human |
|---|---|---|---|
| | Normal SMCs† | hTERT SMCs† | Saphenous Vein |
| Wall Thick. (μm) | 181 ± 75 | 360 ± 76 (P < 0.01) | 370 ± 100* |
| Cell Density ($10^6$ cell/ml) | 118 ± 26 | 135 ± 42 | 164 ± 62‡ |
| Rupture Strength (mm Hg) | 59 ± 55 | 356 ± 64 (P < 0.0005) | 1680 ± 307** |
| Collagen (% dry weight) | 5.1 ± 2.2 | 7.4 ± 1.5 | 48 ± 3.2‡ |

Values are mean ± SD. P values reflect comparisons between normal and hTERT SMC vessels.
†n = 4.
‡n = 3.
*Donovan et al, Journal of Vascular Surgery 12: 531-537 (1990).
**L'Heureux et al, FASEB J. 12: 47-56 (1998).

SMC apoptosis or necrosis in engineered vessels was evaluated by terminal deoxynucleotidyl transferase dUTP nick-end labeling (TUNEL; FIGS. 3C and 3D). hTERT SMC vessels had 11±3% positive nuclei, versus 53±22% positive nuclei for controls (P<0.05). This is consistent with the ability of hTERT SMCs to avoid replicative senescence. Immunostaining for proliferating cell nuclear antigen (PCNA) showed that hTERT SMC vessels had lower cellular proliferation than did normal SMC vessels after 7 weeks of culture (6.6±2.9% vs. 27±26% positive nuclei; P not significant). Decreased PCNA labeling may have resulted from early proliferation of hTERT SMCs followed by contact-mediated quiescence. This is in contrast to control vessels, wherein ongoing SMC death may have stimulated remodeling of the remaining replication-competent cells. The phenotype of hTERT SMCs in engineered vessels after 7 weeks of culture was compared with control SMCs (FIG. 3F). hTERT and normal SMCs expressed similar levels of calponin, SM-MHC, and tropoelastin in engineered tissues. These results indicate that hTERT SMCs maintain cellular viability and differentiated phenotype over prolonged culture periods.

EXAMPLE 2

To determine the feasibility of hTERT expression in vascular SMCs derived from elderly human donors, discarded saphenous vein segments were obtained from the operating room at Duke University Medical Center. Pure cultures of SMCs were obtained using standard explant techniques from a 53 year old and an 83 year old donor. After infection at day 21 of culture, sub-cultured SMCs populations were maintained as Control, Vector, and hTERT populations, and growth kinetics were followed for 150 days (FIG. 4). The lifespan extension of elderly SMCs by hTERT was similar to that observed for 2 year old SMCs, indicating the feasibility of this approach for elderly vascular cells.

Vessels were engineered from control 82 year old SMCs at PD 20, using techniques as described in Example 1. Resulting vessels (n=2) were extremely friable and ruptured at <25 mm Hg. Vessel cellularity was very low (FIG. 5), similar to that observed in vessels engineered from control 2 year old SMCs. hTERT expression in elderly vascular cells is expected to significantly improve the properties of vessels engineered from elderly cells.

Figure 6:
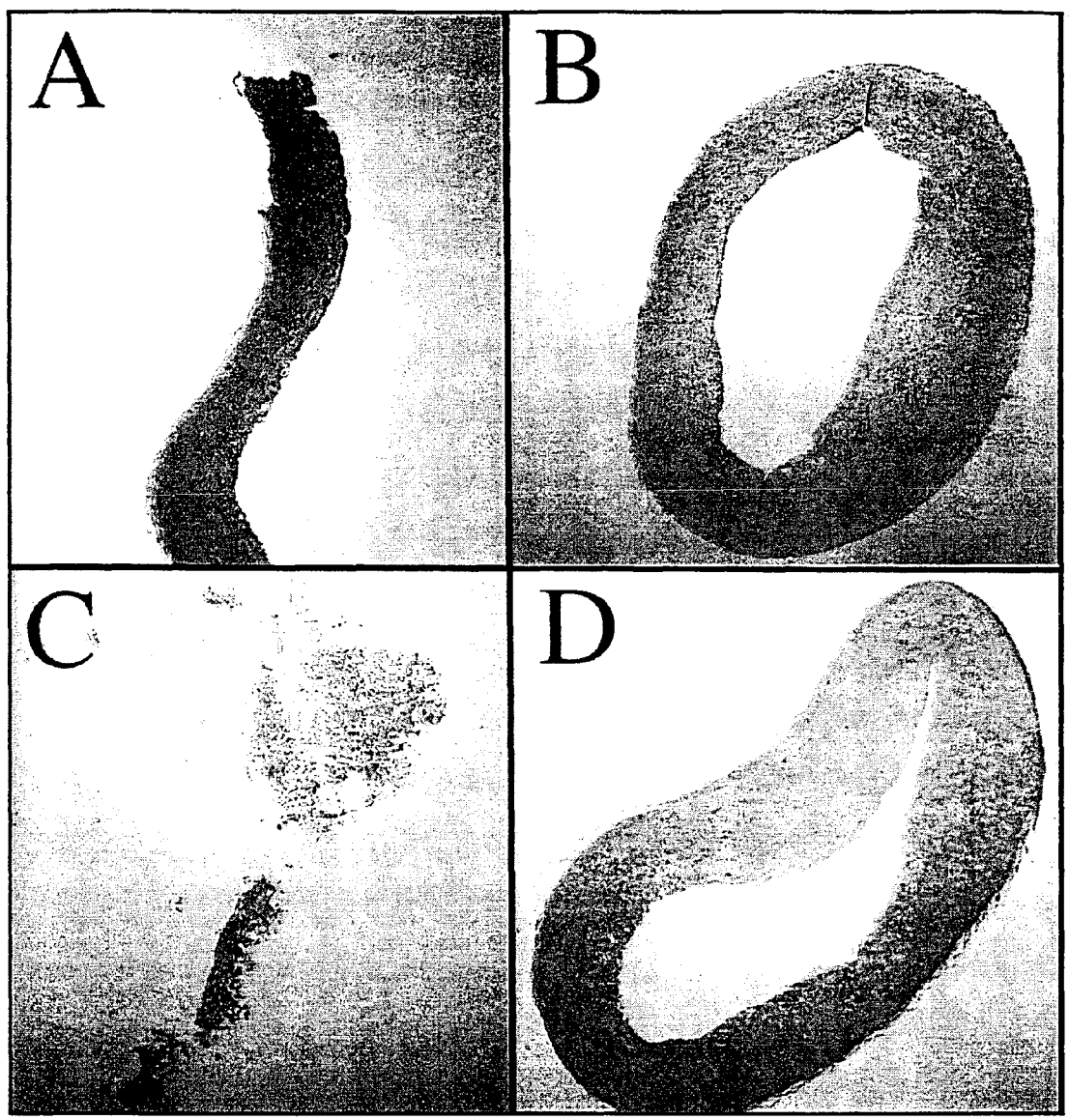
FIGS. 6A-6D. Tissue engineered vessel, elderly vascular cells.

Engineered vessels were cultured from elderly vascular cells, SMC and EC. Control vessels were engineered as described above, using non-infected EC and SMC. Paired hTERT vessels were cultured as described, without hygromycin selection during culture as described. Examples of vessels cultured from 47 year old and 67 year old cells are shown in FIG. 6. Engineered vessels cultured from cells expressing hTERT were significantly stronger, with higher cellularity and improved tissue morphology, as compared to control vessels. These results demonstrate the feasibility of culturing vessels from hTERT-expressing cells. They also demonstrate the significant improvements conferred by hTERT overexpression in elderly vascular cells that are used for tissue engineering.

All documents cited above are hereby incorporated in their entirety by reference.

What is claimed is:

1. A method of producing a vascular graft comprising:
   i) introducing into constituent cells obtained from a human, said constituent cells comprising smooth muscle cells, a construct that comprises a nucleic acid sequence encoding a lifespan extending or immortalizing protein product having telomerase catalytic activity, under conditions such that said nucleic acid sequence is expressed and said protein product is thereby produced, and
   ii) engineering said cells resulting from step (i) into said vascular graft.

2. The method according to claim 1 wherein said constituent cells further comprise cells selected from the group consisting of endothelial cells, epithelial cells, fibroblasts, pericytes, cardiomyocytes and nervous system cells.

3. The method according to claim 1 wherein said constituent cells further comprise non-neonatal endothelial cells.

4. The method according to claim 1 wherein said nucleic acid sequence encodes a catalytic protein subunit of telomerase reverse transcriptase.

5. The method according to claim 4 wherein said telomerase reverse transcriptase is human telomerase reverse transcriptase (hTERT).

6. The method according to claim 1 wherein said protein product does not induce a tumorigenic phenotype.

7. The method according to claim 1 wherein said nucleic acid sequence is present in said construct in operable linkage with a promoter functional in said constituent cells.

8. The method according to claim 7 wherein said promoter is a viral promoter or a tetracycline-inducible promoter.

9. The method according to claim 1 wherein said construct is excisable.

10. The method according to claim 9 wherein said construct is excisable by site-specific recombination.

11. The method according to claim 10 wherein said construct is excisable by Cre recombinase.

12. The method according to claim 1 wherein said construct is introduced into said constituent cells transiently.

13. The method according to claim 12 wherein said transient introduction is effected using an adenoviral vector.

14. The method according to claim 1 wherein said step (ii) comprises seeding cells resulting from step (i) on a tubular support and culturing said cells so that said vascular graft is formed.

15. The method according to claim 14 wherein said tubular support is a gel of denatured collagen, a degradable or non-degradable synthetic scaffold, a fibrillar collagen scaffold or an extracellular matrix scaffold.

16. The method according to claim 1 wherein said step (ii) comprises culturing cells resulting from step (i) so that a cellular sheet is produced and rolling said sheet to form said vascular graft.

17. An isolated vascular graft comprising smooth muscle cells obtained from a human and comprising a recombinant molecule comprising a nucleic acid sequence encoding a lifespan extending or immortalizing protein product having telomerase catalytic activity.

18. The graft according to claim 17 wherein said protein product is hTERT.

19. The method according to claim 1 wherein said vascular graft is an arterial graft.

20. The vascular graft according to claim 17 wherein said vascular graft is an arterial graft.

* * * * *